(12) United States Patent
Oda et al.

(10) Patent No.: US 6,374,662 B1
(45) Date of Patent: Apr. 23, 2002

(54) DEVICES AND METHODS FOR MEASURING ODOR

(75) Inventors: Ryutaro Oda; Motoo Kinoshita, both of Kyoto; Kunihiko Okubo, Shiga; Keiso Kawamoto; Hiroshi Nakano, both of Kyoto, all of (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/479,012

(22) Filed: Jan. 7, 2000

(51) Int. Cl.[7] .................. G01N 33/497; G01N 33/48; B01L 3/00
(52) U.S. Cl. .................. 73/23.34; 422/99; 436/64
(58) Field of Search ................ 73/19.02, 23.3, 73/23.34, 863.21; 422/99; 436/64; 512/5; 600/532

(56) References Cited

U.S. PATENT DOCUMENTS

| 4,257,257 A | * | 3/1981 | Dairaku et al. ............ 73/19.02 |
| 4,772,559 A | * | 9/1988 | Preti et al. .................. 436/64 |
| 5,425,374 A | * | 6/1995 | Ueda et al. .................. 600/532 |
| 5,479,815 A | * | 1/1996 | White et al. .................. 73/23.3 |
| 6,190,613 B1 | * | 2/2001 | Watanabe et al. ............. 422/99 |

* cited by examiner

Primary Examiner—Hezron Williams
Assistant Examiner—Jay L. Politzer
(74) Attorney, Agent, or Firm—Beyer Weaver & Thomas LLP

(57) ABSTRACT

An odor measuring device has a collector tube containing an adsorbent which adsorbs sample components with odor at normal temperatures and desorbs them when heated. Flow routes for a sample gas containing sample components to be detected and an inactive gas are connected through valves to this collector tube. Initially, a sample gas containing sample components with odor is introduced into the collector tube at normal temperature such that the sample components to be detected are adsorbed to the adsorbent. Thereafter, the valves are switched such that the inactive gas is introduced into the collector tube while its temperature is increased by a heater, causing the sample components to be desorbed into the inactive gas and to be transported into an odor sensor. If odor sensors requiring oxygen for detection are used, an oxygen-containing gas such as air is mixed into the inactive gas after the latter has passed through the collector tube such that deterioration of the adsorbent by oxidation can be prevented.

11 Claims, 2 Drawing Sheets

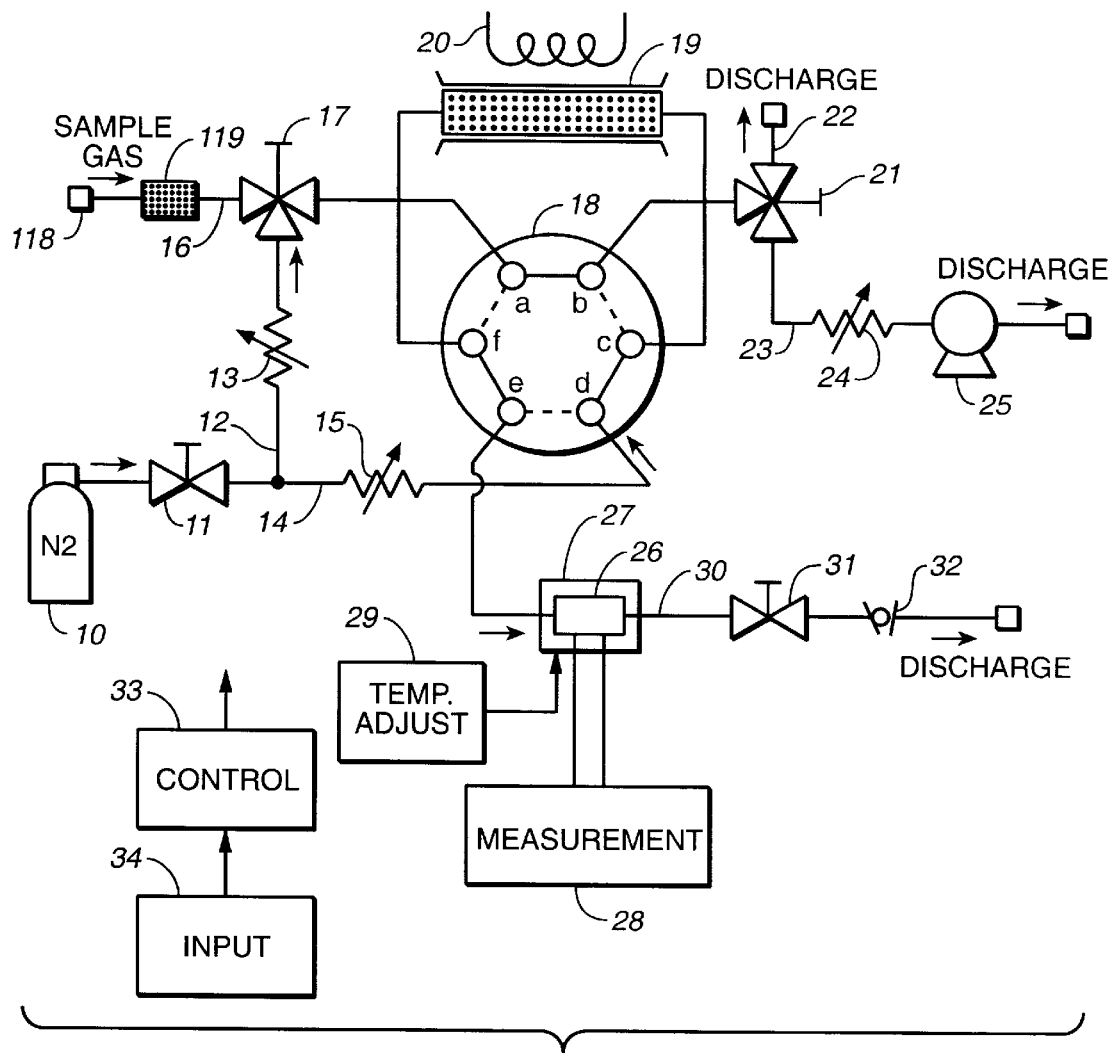
FIG._1
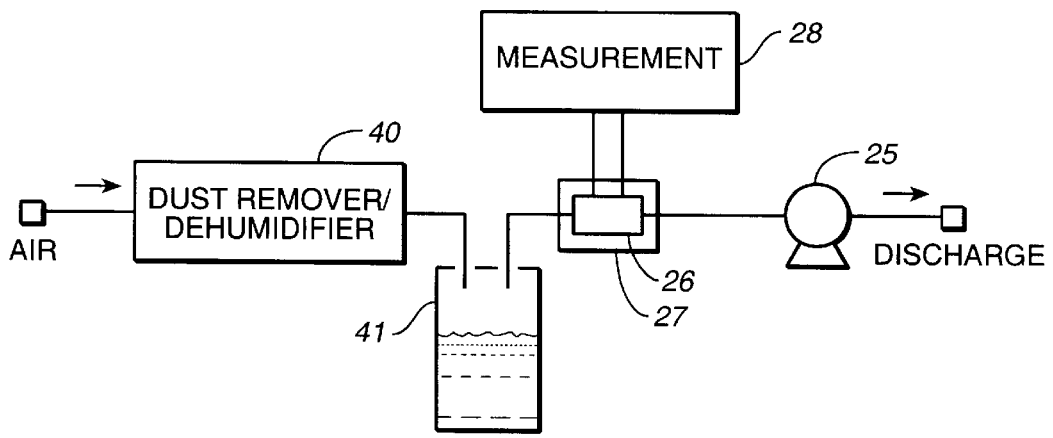
FIG._3
(PRIOR ART)

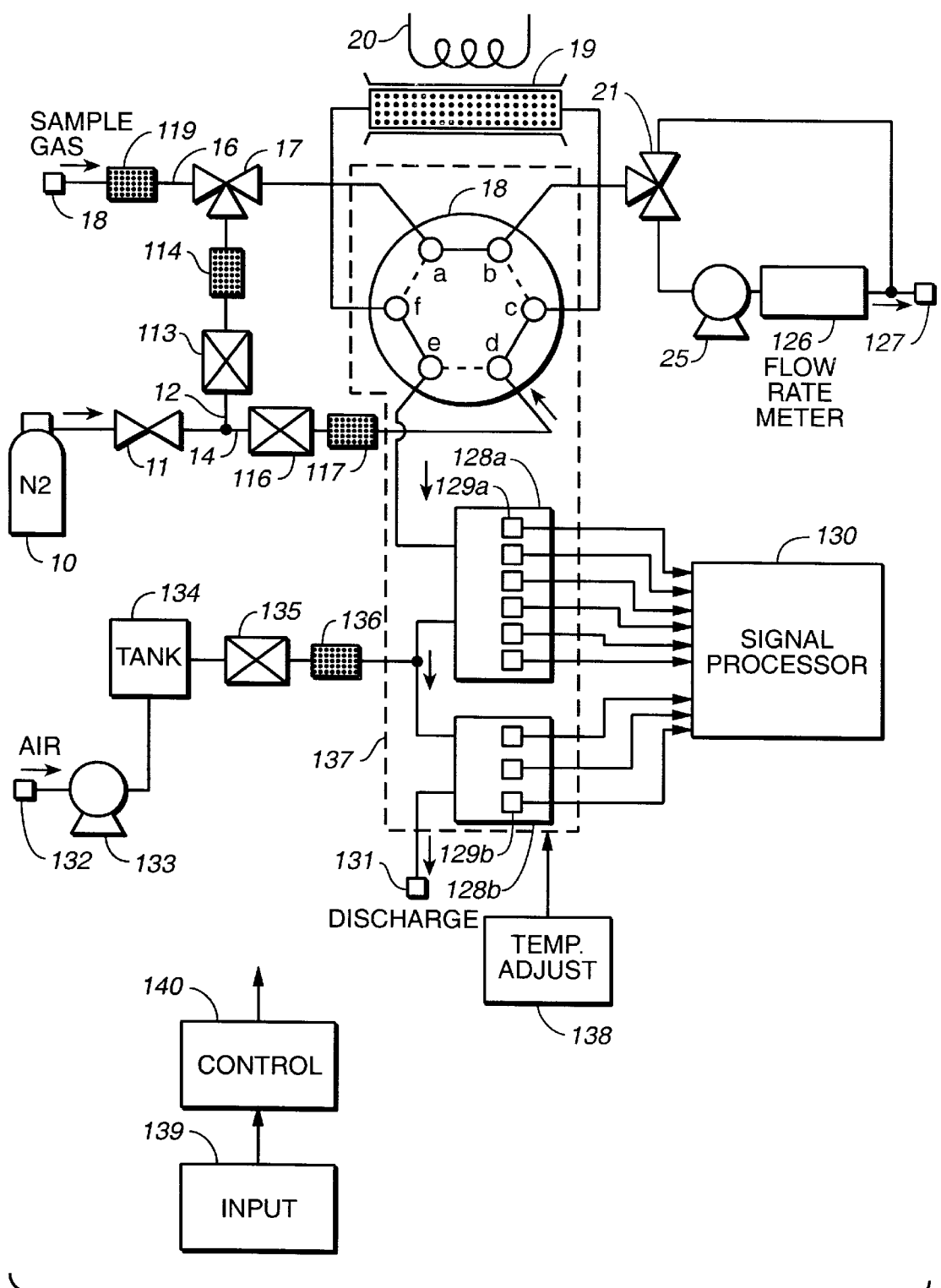
FIG._2

DEVICES AND METHODS FOR MEASURING ODOR

BACKGROUND OF THE INVENTION

This invention relates to devices and methods for measuring odor, or odorous components in a sample gas, by means of an odor sensor which is a kind of gas sensor. Such odor measuring devices may be found useful in many fields of application such as the quality control of foods and perfumes, the quantitative analysis of public nuisance due to odor, the fire prevention by detecting a burning odor, and even in the police work such as in the tracing and identification of a suspected person or discovery of illegal chemicals.

An odor sensor is adapted to electrically or optically measure a change which takes place in the sensor when an odorous component in air or in a sample which is supplied thereto becomes attached to the sensor's odor-sensitive surface. Odor sensors using semiconducting oxides and electrically conductive polymers have been known.

FIG. 3 shows an example of a prior art odor measuring device using such an odor sensor. When a pump 25 is activated, purified air deprived of floating dust particles and water components by a dust-removing and dehumidifying unit 40 is introduced into a sample container 41 storing therein a sample liquid which contains an odorous component, and a sample gas containing the odorous component is supplied from the sample container 41. As this sample gas containing the odorous component is introduced into a flow cell 27 which contains an odor sensor 26 therein, the odorous component is adsorbed to an odor-sensitive film of the odor sensor 26, causing a change in the resistance between electrodes of the odor sensor 26. There is a measuring unit 28 which serves to measure this change, and the sample gas leaving the flow cell 27 is discharged through the pump 25. The use of purified air as the carrier gas for the odorous component serves not only to prevent corrosion of the odor-sensitive film and the electrodes but also to reduce erroneous response of the odor-sensitive film due to unwanted substances which may also become adsorbed thereto.

Odor sensors using an odor-sensitive film comprising an electrically conductive polymer are coming to be used recently, but their sensitivity is affected as the odor-sensitive film become oxidized by the oxygen gas in air. If such an odor-sensor is used in an odor measuring device as described above, the odor-sensitive film is gradually oxidized due to the oxygen component in the sample gas, making it difficult with the passage of time to obtain results with high repeatability. Since the oxidation of a conductive polymer film is accelerated particularly in an environment with high humidity, the deterioration of the odor-sensitive film becomes a severe problem when the measurement is carried out at a high temperature or the odor sensor is operated at a high temperature in order to remove the odorous component which has become adsorbed. In other words, the useful lifetime of the odor-sensitive film is short, and it must be replaced frequently. This naturally adds not only to the cost of operation but also to the time required for the measurement.

Another problem to be considered is that a process for gas condensation by thermal desorption is frequently carried out, when the odorous component is at a relatively low concentration in a sample gas, in order to increase the concentration of the target component to be measured. By the thermal desorption method, the sample gas is passed through a condenser tube filled with a material which mainly adsorbs the target component. After the target component has been sufficiently adsorbed thereto, a carrier gas is passed through this condenser tube while its temperature is raised suddenly such that the once adsorbed target component is desorbed quickly and is introduced into the sensor at a higher concentration.

In the case of a sensor using a semiconducting oxide such as tin oxide as the odor-sensitive film, what is actually measured is a change in the conductivity of the semiconducting oxide due to the oxidation-reduction reaction between oxygen and a reductive gas adsorbed to the semiconducting oxide. Thus, the carrier gas for transporting the target component to be measured must be one which contains oxygen, such as air. In other words, the agent which fills the condenser tube must be of a kind which does not degenerate although it is heated to a high temperature in the presence of oxygen. In general, different agents must fill the condenser tube for the adsorption of different target components to be measured. Thus, there is usually only a limited number of agents that can be used. For example, ordinarily used agents comprising carbon will deteriorate significantly if heated in the presence of oxygen and hence cannot be used in the condenser tube of an odor measuring device.

SUMMARY OF THE INVENTION

It is therefore an object of this invention to provide an improved odor measuring device capable of preventing or reducing the deterioration of its sensor due to oxidation.

It is another object of this invention to provide such an odor measuring device for which agents of many different kinds can be used when an odor sensor such as comprising a semiconducting oxide requiring oxygen for the detection of the odorous component and a condenser device using the thermal desorption method are combined.

It is additionally an object of this invention to provide methods of measuring odor, or components with odor in a sample gas, by using such devices.

An odor measuring device according to this invention, with which the first of the above objects can be accomplished, may be characterized as comprising a collector tube containing an adsorbent which adsorbs sample components with odor at normal temperatures and desorbs these sample components when heated. Flow routes for a sample gas containing sample components to be detected and an inactive gas are connected through switchable valves to this collector tube. Initially, a sample gas containing sample components with odor is introduced into the collector tube at normal temperature such that the sample components to be detected are adsorbed to the adsorbent. Thereafter, the valves are switched and the gas flow routes are changed such that the inactive gas is introduced into the collector tube while its temperature is increased by a heater, causing the sample components to be desorbed into the inactive gas and to be transported thereby into an odor sensor.

The second of the above objects can be accomplished by further providing means for mixing an oxygen-containing gas such as air into the inactive gas after the latter has passed through the collector tube. With a device thus structured, the carrier gas which transports the sample components to the odor sensor is mostly inactive but also contains some oxygen. Thus, odor sensors with semiconducting oxides which require oxygen for the detection may be used but since the oxygen-containing gas is mixed to the inactive gas after the latter has passed the collector tube, the adsorbent in the collector tube does not come into contact with the oxygen-containing gas and hence is not oxidized.

When sensors of both types requiring and not requiring the existence of oxygen for detection, such as sensors with electrically conductive polymers and semiconducting oxides, are used together, the odor detecting means may be divided into a first part consisting of sensors not requiring oxygen for detection and a second part consisting of those requiring oxygen for detection and the oxygen-containing gas may be mixed to the inactive gas after the latter has passed through the first part. With the odor detecting means thus structured, the oxygen-containing gas which is mixed in does not come into contact with the sensors of the first part such as those using conducting polymers and hence deterioration of such polymers by oxidation can be prevented.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a flow route diagram of an odor measuring device embodying this invention;

FIG. 2 is a flow route diagram of another odor measuring device embodying this invention; and FIG. 3 is a schematic block diagram of a prior art odor measuring device.

Throughout herein, like or substantially equivalent components are indicated by same numerals and may not necessarily be described repetitiously for simplifying the description.

DETAILED DESCRIPTION OF THE INVENTION

The invention will be described next by way of examples.

FIG. 1 shows schematically the structure of an odor measuring device embodying this invention. A constant-pressure valve 11 is provided to the outlet of a nitrogen gas container 10 containing pure nitrogen gas, and the flow route on the downstream side of this constant-pressure valve 11 is branched into a first nitrogen flow route 12 containing a needle valve 13 and a second nitrogen flow route 14 containing another needle valve 15. The first nitrogen flow route 12 and a sample flow route 16, which is connected to a sample gas source 118 through a PTFE membrane filter 119 for eliminating dust particles, are selectively connected by means of a three-way valve 17 (the "first three-way valve") to one of the ports (Port a) of a six-way valve 18 (with six ports a, b, c, d, e and f). The two positions at which the six-way valve 18 can be set are respectively shown by solid and broken lines in FIG. 1. The second nitrogen flow route 14 is connected to Port d of the six-way valve 18. A collector tube 19 equipped with a heater 20 is connected between Ports c and f An adsorbing agent such as carbon adsorbent that may be suitable for the target component to be measured fills the collector tube 19. Port b is connected selectively to a first discharge route 22 or to a second discharge route 23 which contains a needle valve 24 and a pump 25 through another three-way valve 21 (the "second three-way valve"). Port e is connected to a flow cell 27 containing an odor sensor 26 with an odor-sensitive film and electrode (not shown). On the downstream side of the flow cell 27 is a third discharge route 30 containing a valve 31 and a check valve 32. A measuring device 28 is provided for measuring the resistance between the electrodes of the odor sensor 26. The temperature of the flow cell 27 is adapted to be varied within a specified range by means of a temperature adjusting device 29.

Operations of various components described above such as the three-way valves 17 and 21, the six-way valve 18, the pump 25, the heater 20 and the temperature adjusting device 29 are controlled according to a specified program by a control unit 33 which is provided also with an input device 34. It is preferable to use PTFE tubes for various flow routes because of smaller adsorption of sample components.

Next, various operations of the device are individually explained.

For the collection of a sample component, the control unit 33 adjusts the first three-way valve 17 such that the sample gas route 16 will connect to Port a of the six-way valve 18. The six-way valve 18 is set in the position shown in FIG. 1 by broken lines, and the second three-way valve 21 is adjusted such that Port b of the six-way valve 18 connects to the second discharge route 23. As the pump 25 is activated, a sample gas, with a target component contained in pure air and introduced into the sample flow route 16, passes through the first three-way valve 17, the six-way valve 18 and the collector tube 19 (from the left to the right with reference to FIG. 1) and is discharged from the outlet of the second discharge route 23 through the six-way valve 18 again, the second three-way valve 21 and the needle valve 24. During the operation above, the heater 20 remains inactive and hence the collector tube 19 is maintained at a normal temperature. Thus, the target component in the sample gas is adsorbed by an adsorbent which fills the collector tube 19. In the meantime, the gas pressure at the outlet of the nitrogen gas container 10 is high, and the nitrogen gas which is supplied through the second nitrogen flow route 14 is led to the flow cell 27 through the six-way valve 18 and discharged from the outlet of the third discharge route 30. The flow rate of the nitrogen gas is appropriately controlled by means of the needle valve 15. Thus, the odor sensor 26 is maintained in an atmosphere of nitrogen gas.

After the sample gas is passed through the collector tube 19 for a specified length of time, the control unit 33 switches the connection of the three-way valves 17 and 21 such that the first nitrogen flow route 12 is connected to Port a of the six-way valve 18 and Port b of the six-way valve 18 is connected to the first discharge route 22. As a result, it becomes the nitrogen gas supplied from the nitrogen gas container 10, instead of the sample gas, that passes through the first nitrogen flow route 12, the first three-way valve 17, the six-way valve 18, the collector tube 19, again the six-way valve 18 and the second three-way valve 21 and is discharged from the outlet of the first discharge route 22. Thus, the portion of the sample gas which may be remaining in the route described above will be pushed out by the nitrogen gas. During this operation, the collector tube 19 is maintained at the normal temperature and hence the target component which has been adsorbed to the adsorbent in the collection tube 19 remains adsorbed. Since the flow of the nitrogen gas continues in the meantime, the odor sensor 26 remains to be in an atmosphere of nitrogen gas.

After the nitrogen gas is caused to flow through the collector tube 19 for a specified length of time, the control unit 33 switches the position of the six-way valve 18 as shown by solid lines in FIG. 1. As a result, a flow route is established through the second nitrogen flow route 14, the six-way valve 18, the collector tube 19, again the six-way valve 18, the flow cell 27 and the third discharge route 30.

The heater 20 is switched on under this condition so as to heat the collector tube 19 quickly. The target component which has remained adsorbed to the adsorbent inside the collector tube 19 is thereby desorbed and transported to the flow cell 27 by the nitrogen gas which now flows through the collector tube 19 in the reverse direction (that is, from the right to the left with reference to FIG. 1). The flow cell 27 is maintained at this time at a temperature of about 40° C. by means of the temperature adjusting device 29. As the nitrogen gas carrying the target component passes through the flow cell, the target component becomes adsorbed to the odor-sensitive film of the odor sensor 26, changing the resistance between the electrodes of the odor sensor 26. The measuring device 28 measures this change in the resistance and thereby detects the target component.

For cleaning the odor sensor 26 after the operations described above for the detection are completed, the control unit 33 switches the position of the six-way valve 18 in the way shown by broken lines in FIG. 1, thereby causing pure nitrogen gas to flow through the flow cell 27. The control unit 33 also raises the temperature of the flow cell 27 to a specified level through the temperature adjusting device 29. As the temperature of the odor sensor 26 is raised, the target components and other contaminants adsorbed to the odor-sensitive film are desorbed and carried away by the flowing nitrogen gas. The odor-sensitive film of the odor sensor 26 is thus recovered to the original condition, ready for another detection operation.

When the odor measuring device is not being used, the three-way valve 17 and 21 and the valve 31 may be all closed so as to prevent external air from invading the interior of the device, keeping the interior in the condition wherein all the flow routes are filled with nitrogen gas. This serves to prevent the oxidation of the odor-sensitive film.

Although the routines described above are normally carried out automatically according to a preliminarily prepared program, it is preferable to make the program adjustable such that the timing for the switching of various valves and the temperature of the heater 20 may be varied according to the kind of target component to be detected. Such adjustments may be carried out by a user through the input device 34. It goes without saying that the operations can be made manually controllable.

FIG. 2 shows schematically the structure of another odor measuring device embodying this invention. Because a portion of this odor measuring device is structured similarly to the one described above with reference to FIG. 1, those of the components which are similar or substantially alike are indicated by the same numerals and may not necessarily be described repetitiously for the convenience of description.

As shown in FIG. 2, a constant-pressure valve 11 is provided to the outlet of a nitrogen gas container 10 containing pure nitrogen gas, and the flow route on the downstream side of this constant-pressure valve 11 is branched into a first nitrogen flow route 12 containing a flow rate controller 113 such as a mass flow controller and a molecular sieve filter 114 and a second nitrogen flow route 14 containing another flow rate controller 116 and another molecular sieve filter 117. The first nitrogen flow route 12 and a sample flow route 16, through which a sample gas containing target components to be measured ("sample components") is introduced, are selectively connected by means of a three-way valve 17 (the "first three-way valve") to one of the ports (Port a) of a six-way valve 18 (with six ports a, b, c, d, e and f). The two positions at which the six-way valve 18 can be set are again respectively shown by solid and broken lines. The second nitrogen flow route 14 is connected to Port d of the six-way valve 18. A collector tube 19 equipped with a heater 20 is connected between Ports c and f An adsorbing agent such as carbon adsorbent that may be suitable for the sample components to be measured fills the collector tube 19. Port b is connected to a discharge outlet 127 selectively either directly or through a pump 25 and a flow rate meter 126 through another three-way valve 21 (the "second three-way valve"). Port e is connected to a first flow cell 128a which is provided with a plurality of odor sensors 129a and is connected on its downstream side to a second flow cell 128b provided also with a plurality of odor sensors 129b. Another discharge outlet 131 is connected to the downstream side of the second flow cell 128b. The odor sensors 129a in the first flow cell 128a have odor-sensitive films comprising different electrically conductive polymers having different detection sensitivities against various target sample components to be detected. The odor sensors 129b in the second flow cell 128b have odor-sensitive films comprising different semiconducting oxides having different detection sensitivities against various components. Output signals from these odor sensors 129a and 129b are introduced into a signal processor 130 for carrying out various operations such as identification and classification of various odorous components.

Air, sucked in from an air inlet 132 by means of an air pump 133, is stored in an air tank 134 in a compressed condition. The air tank 134 is connected to the flow route between the first flow cell 128a and the second flow cell 128b through an air flow rate controller 135 and an active charcoal filter 136 for eliminating impurities. The six-way valve 18 and the flow cells 128a and 128b are all contained in a thermostatic container 137 of which the temperature is controlled by a temperature adjusting device 138.

Operations of various components described above such as the three-way valves 17 and 21, the six-way valve 18, the pumps 25 and 133, the heater 20 and the temperature adjusting device 138 are controlled according to a specified program by a control unit 140 which is provided also with an input device 139. It is preferable to use PTFE tubes for various flow routes because of smaller adsorption of sample components. For preventing oxygen from mixing with the nitrogen gas, however, it is further preferable to use metallic tubes such as stainless steel tubes in the first nitrogen flow route 12 from the outlet of the nitrogen gas container 10 to the first three-way valve 17 and the second nitrogen flow route 14 to Port d of the six-way valve 18 and stainless steel tubes with inner surface covered with phased silica made inactive for the flow route from Port c of the six-way valve 18 to the collector tube 19.

Next, various operations of the device are individually explained.

For the collection of sample components, the control unit 140 adjusts the first three-way valve 17 such that the sample gas source 118 will connect to Port a of the six-way valve 18. The six-way valve 18 is set in the position shown in FIG. 2 by broken lines, and the second three-way valve 21 is switched such that Port b of the six-way valve 18 connects to the pump 25. As the pump 25 is activated, a sample gas, with target odorous components contained in pure air and sucked in from the sample gas source 118, passes through the first three-way valve 17 and the six-way valve 18 and is introduced into the collector tube 19 (from the left to the right with reference to FIG. 2) after having relatively large contaminants such as dust particles removed by the membrane filter 119. It is then discharged from the discharge outlet 127 through the six-way valve 18 again, the second three-way valve 21, the pump 25 and the flow rate meter 126. The control unit 140 controls the suction power of the pump 25 such that the flow rate detected by the flow rate meter 126 will come to a specified level. As the sample gas passes through the collector tube 19, the heater 20 is not activated. Thus, the target components in the sample gas are adsorbed to the adsorbent filling the collector tube 19. In the meantime, the gas pressure at the outlet of the nitrogen gas container 10 is high, and the nitrogen gas which is supplied through the second nitrogen flow route 14 is led to the first and second flow cells 128a and 128b and is discharged from the discharge outlet 131. Thus, the odor sensors 129a and 129b are maintained in an atmosphere of nitrogen gas. As will be described below, air from the air tank 134 may also be supplied to the second flow cell 128b, mixed with the nitrogen gas from the nitrogen gas source 10.

After the sample gas is passed through the collector tube 19 for a specified length of time, the control unit 140 switches the connections of the three-way valves 17 and 21 such that the first nitrogen flow route 12 is connected to Port a of the six-way valve 18 and Port b of the six-way valve 18 is connected directly to the discharge outlet 127. As a result, it becomes the nitrogen gas 30 supplied from the nitrogen gas container 10, instead of the sample gas, that passes through the first nitrogen flow route 12, the first three-way valve 17, the six-way valve 18, the collector tube 19, again the six-way valve 18 and the second three-way valve 21 and is discharged from the discharge outlet 127. Thus, the portion of the sample gas which may be remaining in the route described above, inclusive of the collector tube 19, will be pushed out by the nitrogen gas. During this operation, the collector tube 19 is maintained at a normal temperature and hence the target components which have been adsorbed to the adsorbent in the collection tube 19 remain in the adsorbed condition. Since the nitrogen gas is kept in a very dry condition, the water component which has been adsorbed to the adsorbent in the collector tube 19 is also mostly carried away by the nitrogen gas. In this manner, the removal of water components can also be achieved to a certain degree.

After the nitrogen gas is caused to flow through the collector tube 19 for a specified length of time, the control unit 140 switches the six-way valve 18 to the position shown by solid lines in FIG. 2. As a result, a flow route is established through the second nitrogen flow route 14, the six-way valve 18, the collector tube 19, again the six-way valve 18, the first flow cell 128a, the second flow cell 128b and the discharge outlet 131. The heater 20 is switched on under this condition so as to heat the collector tube 19 quickly. The target components which have remained adsorbed to the adsorbent inside the collector tube 19 are thereby desorbed and transported to the first flow cell 128a by the nitrogen gas which now flows through the collector tube 19 in the reverse direction (that is, from the right to the left with reference to FIG. 2). The program for the operation of various components is so made that the volume of the nitrogen gas which passes through the collector tube 19 from the time when the heating of the collector tube 19 is started until the desorption of the target component from the adsorbent is nearly completely ended will be smaller than the volume of the sample gas which passes through the collector tube 19 as described above. In this manner, a gas with target components in a condensed state can be introduced into the first flow cell 128a.

As the temperature of the collector tube 19 is thus varied, the flow resistance is thereby affected and the flow rate of the nitrogen gas into the first flow cell 128a may change. If this happens, the detection by the odor sensors 129a may turn out to be erroneous. If a mechanically controlled mass flow controller of the so-called secondary pressure varying type is used in the place of the flow rate controller 116, for example, the flow rate of the nitrogen gas passing therethrough can be maintained at a constant rate although the flow route resistance through this flow route may change. In order that this mass flow controller should operate normally, the difference in pressure between its inlet side and its outlet side must be larger than a certain minimum value. Thus, the pressure set for the constant-pressure valve 11, the inner diameter of the flow tubes, the flow rate of the air mixed in through the air flow rate controller 135, etc. should be determined such that a large enough pressure difference will be obtained between both sides of the flow rate controller 116. In this manner, the flow rate of the nitrogen gas can be dependably controlled and there will be no reverse flow of the mixed gas from the position where air is mixed towards the first flow cell 128a.

As the nitrogen gas containing the target sample components passes through the first flow cell 128a, these components are adsorbed to the odor-sensitive film of the odor sensors 129a comprised of electrically conductive polymers, and the resistance between the electrodes of the odor sensors 129a undergoes a change. Detection signals generated by this change in the resistance are sequentially transmitted to the signal processor 130.

The air, which has been compressed by the air pump 133 and stored in the air tank 134, is caused to flow at an appropriate flow rate adjusted by the air flow rate controller 135 and after unwanted components which may cause external disturbance to the measurement are removed by means of the active charcoal filter 136, it is mixed with the nitrogen gas containing the sample components after it has passed through the first flow cell 128a. Since air contains oxygen gas, the nitrogen gas coming from the first flow cell 128a is now mixed with oxygen gas. That is, the sample components enter the second flow cell 128b together with oxygen gas. The molecules of this oxygen gas are adsorbed to the odor-sensitive film made of a semiconducting oxide and an oxidation-reduction reaction takes place with the molecules of the sample components. This affects the conductivity of the odor sensors 129b and the resistance between their electrodes changes. Signals which indicate such changes in the resistance are also transmitted to the signal processor 130 sequentially.

The plurality of odor sensors 129a and 129b each have different characteristics. Thus, there may be a situation wherein a large detection signal is outputted from a certain odor sensor but no detection signal is outputted from the other odor sensors against a certain sample component. Thus, the signal processor 130 relies on all of the plurality of detection signals thus received to carry out a selected multi-variable analysis such as the so-called principal component analysis or the stage-wise cluster analysis to identify or classify the odorous components in a summary manner.

During the period of such an analysis, the six-way valve 18, the first and second flow cells 128a and 128b and the flow routes connecting them are all maintained by means of the temperature adjusting device 138 at a constant temperature (such as 40° C.) higher than the room temperature. This is so as to reduce the effects of variations in the environmental temperature on the odor sensors 129a and 129b and also to prevent compounds with high boiling points from becoming deposited inside the flow routes to thereby adversely affect the stability of detection sensitivity.

The series of operations described above related to analysis may be carried out automatically according to a program which may be preliminarily set in the control unit 140. It is preferable, however, that the program be so prepared that certain parameters such as the timing for switching various valves and the temperature of the heater 20 can be set by the user through the input device 139 according to the kinds of the sample components. The invention also includes applications wherein the user is required to keep inputting commands through the input device 139.

Although FIG. 2 shows an example wherein air is mixed in on the upstream side of the second flow cell 128b, this may be altered such that pure oxygen gas is mixed, instead of air, with the nitrogen gas. Since the volume of gas to be mixed can be reduced significantly if pure oxygen is used instead of air, the rate at which the sample components are diluted can be reduced and the detection sensitivity of the odor sensors 129b can be thereby improved.

The types of odor sensors to be used in the first and second flow cells 128a and 128b do not limit the scope of the invention. Odor sensors with synthetic bimolecular films covering a quartz oscillator may be used. In general, odor sensors of the kind not requiring oxygen for the detection should more advantageously be placed inside the first flow cell 128a from the point of view of detection sensitivity. This is firstly because the gas which flows through the second flow cell 128b becomes diluted because of the air which is mixed in and the concentrations of the sample components become reduced, and secondly because the temporal spreads of sample components in the direction of the flow route as the gas containing the sample components flows are smaller inside the first flow cell 128a because it is closer to the collector tube 19 and the concentrations of the sample components are relatively high.

It now goes without saying that many modifications and variations are possible within the scope of this invention. According to this invention, in summary, the heating for desorption of the sample components takes place after the interior of the collector tube is replaced by an inactive gas and oxygen is introduced into the flow route connecting the collector tube and odor sensors which require oxygen for the detection of semiconducting oxides. Thus, oxygen gas does not contact the agent inside the collector tube when this agent is at a high temperature and hence even materials of which the characteristic may be deteriorated by oxidation can be used as the agent. In other words, a wider range of adsorbents can be used inside the collector tube according to this invention.

The invention also discloses the use together of both sensors using semiconducting oxides and sensors which should preferably be kept away from oxygen. Thus the number of sample components that can be measured is increased significantly.

What is claimed is:

1. A device for measuring odor, said device comprising:
    odor detecting means for detecting odor;
    gas supplying means for supplying an inactive gas without containing oxygen to said odor detecting means;
    sample supplying means for supplying a sample gas containing sample components with odor to said odor detecting means;
    adsorbing means containing an adsorbent which adsorbs sample components with odor at normal temperatures and desorbs said sample components when heated;
    first flow route switching means for introducing selectively either a sample gas from said sample supplying means or said inactive gas from said gas supplying means to said odor detecting means; and
    second flow route switching means connected between said first flow route switching means and said odor detecting means and also to said adsorbing means for introducing said inactive gas from said gas supplying means into said odor detecting means selectively either without passing through said adsorbing means or after passing through said adsorbing means, said odor detecting means serving to detect said sample components by detecting odor thereof.

2. The device of claim 1 further comprising a control unit which serves to cause said sample gas to flow through said adsorbing means to thereby cause said sample components to adsorb to said adsorbent and only said inactive gas to flow through said odor detecting means, and thereafter to switch said first flow route switching means and said second flow route switching means to thereby cause said sample components to be desorbed from said adsorbent into said inactive gas and transported with said inactive gas into said odor detecting means.

3. The device of claim 1 further comprising a heater for heating said adsorbent and thereby causing desorption of said sample components from said adsorbent.

4. The device of claim 2 further comprising a heater which is controlled by said control unit for heating said adsorbent and thereby causing desorption of said sample components from said adsorbent.

5. A method of measuring odor of a sample gas, said method comprising the steps of:
    causing said sample gas to flow through an adsorbent and to thereby cause sample components with odor in said sample gas to adsorb to said adsorbent while causing only an inactive gas without containing oxygen to flow through odor detecting means for detecting said sample components; and
    thereafter causing said sample components to be desorbed from said adsorbent into said inactive gas and transported into said odor detecting means, said sample components being desorbed and transported into said odor detecting means by the step of switching flow routes of said sample gas and said inactive gas such that said inactive gas is caused to flow through said adsorbent and by the step of heating said adsorbent.

6. A device for measuring odor, said device comprising:
    odor detecting means for detecting odor;
    gas supplying means for supplying an inactive gas to said odor detecting means;
    sample supplying means for supplying a sample gas containing sample components with odor to said odor detecting means;
    adsorbing means containing an adsorbent which adsorbs sample components with odor at normal temperatures and desorbs said sample components when heated;
    flow route switching means connected to said gas supplying means, said sample supplying means, said odor detecting means, said adsorbing means and a discharge outlet for selectively switching between a first flow route through which a sample gas from said sample supplying means is introduced into said adsorbing means and is thereafter discharged externally through said discharge outlet and a second flow route through which said inactive gas from said gas supplying means is introduced into said adsorbing means; and
    mixing means connected to said odor detecting means for mixing an oxygen-containing gas which comprises oxygen into said inactive gas after said inactive gas has passed through said adsorbing means and thereby obtaining a gas mixture; said odor detecting means serving to detect said sample components contained in said gas mixture by detecting odor thereof.

7. The device of claim 6 further comprising a control unit which serves:

to cause said sample gas to flow through said adsorbing means to thereby cause said sample components to adsorb to said adsorbent;

to switch said flow route switching means to thereby cause said sample components to be desorbed from said adsorbent into said inactive gas;

to thereafter cause said oxygen-containing gas to be mixed to said sample components and then to be introduced into said odor detecting means.

8. The device of claim 6 further comprising a heater for heating said adsorbent and thereby causing desorption of said sample components from said adsorbent.

9. The device of claim 7 further comprising a heater which is controlled by said control unit for heating said adsorbent and thereby causing desorption of said sample components from said adsorbent.

10. A method of measuring odor of a sample gas, said method comprising the steps of:

causing said sample gas to flow through an adsorbent and to thereby cause sample components with odor in said sample gas to adsorb to said adsorbent;

thereafter causing said sample components to be desorbed from said adsorbent into an inactive gas by switching flow routes of said sample gas and said inactive gas to thereby introduce said inactive gas into said adsorbent; and thereafter obtaining a gas mixture by causing an oxygen-containing gas which comprises oxygen to be mixed to said sample components and said inactive gas and then introducing said gas mixture into odor detecting means for detecting said sample components.

11. The method of claim 10 wherein said sample components are desorbed and transported into said odor detecting means by the step of switching flow routes of said sample gas and said inactive gas such that said inactive gas is caused to flow through said adsorbent and by the step of heating said adsorbent.

* * * * *